(12) United States Patent
Kraemer et al.

(10) Patent No.: US 7,708,560 B2
(45) Date of Patent: May 4, 2010

(54) SYSTEM AND METHOD FOR MANUFACTURING DENTAL PROSTHESES

(75) Inventors: Michael A. Kraemer, Landsberg am Lech (DE); Michael K. Schaaf, Herrsching (DE); Thomas Sprengart, Landsberg am Lech (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 11/283,629

(22) Filed: Nov. 21, 2005

(65) Prior Publication Data

US 2006/0111806 A1    May 25, 2006

(30) Foreign Application Priority Data

Nov. 22, 2004   (EP)   ................................. 04027709

(51) Int. Cl.
*G06F 19/00*   (2006.01)
*A61C 5/10*   (2006.01)
(52) U.S. Cl. ........................ 433/223; 700/117; 700/182
(58) Field of Classification Search .................... 700/95, 700/97, 98, 159, 160, 182, 115, 116, 117, 700/118; 623/901; 433/49, 163, 223; 264/16, 264/17, 19
See application file for complete search history.

(56) References Cited

U.S. PATENT DOCUMENTS

| | | | | |
|---|---|---|---|---|
| 5,027,509 A * | 7/1991 | Barben et al. | ............... | 29/895.3 |
| 5,684,708 A * | 11/1997 | Kondou et al. | ............... | 700/179 |
| 6,287,121 B1 | 9/2001 | Guiot et al. | | |
| 6,454,568 B1 * | 9/2002 | Beuschel et al. | ............ | 433/163 |
| 7,178,731 B2 * | 2/2007 | Basler | .................... | 235/462.01 |
| 2002/0182566 A1 * | 12/2002 | Beuschel et al. | ............ | 433/163 |

FOREIGN PATENT DOCUMENTS

| | | |
|---|---|---|
| DE | 102 33 314 A1 | 2/2004 |
| EP | 1 088 526 A2 | 4/2001 |
| WO | WO 95/15731 A1 | 6/1995 |
| WO | WO 96/37163 A1 | 11/1996 |
| WO | WO 98/44865 | 10/1998 |
| WO | WO 01/37756 A1 | 5/2001 |
| WO | WO 01/97707 A1 | 12/2001 |
| WO | WO 2004/016189 * | 2/2004 |

\* cited by examiner

*Primary Examiner*—Charles R Kasenge

(57) ABSTRACT

The present invention is related to systems and methods for manufacturing dental prostheses, such as bridges and crowns. In particular, the present invention is directed to novel methods for managing machining jobs for manufacturing dental prostheses in a system having a plurality of machining devices.

18 Claims, 6 Drawing Sheets

SYSTEM AND METHOD FOR MANUFACTURING DENTAL PROSTHESES

CROSS REFERENCE TO RELATED APPLICATIONS

This application claims priority from European Serial No. 04027709.7, filed Nov. 22, 2004.

TECHNICAL FIELD

The present invention is related to systems and methods for manufacturing dental prostheses, such as bridges and crowns. In particular, the present invention is directed to novel methods for managing machining jobs for manufacturing dental prostheses in a system having a plurality of machining devices.

BACKGROUND OF THE INVENTION

Prostheses are commonly used in the dental industry for replacing or reconstructing teeth. Generally, such dental prostheses can be in the form of implants, crowns, bridges, onlays and inlays. Since such prostheses have to be designed precisely in order to ensure proper fit, manufacturing methods for such products have to meet certain criteria in terms of accuracy in designing and machining. It is recognized in the art that computer aided design (CAD) and computer aided manufacturing (CAM) can be viable options for providing flexibility, ease and accuracy in designing and manufacturing such prostheses.

For example, U.S. Pat. No. 6,287,121 describes a device for determining the shape of a duplicate of a remaining tooth area to be provided with a dental prosthesis and an arrangement for producing the dental prosthesis. The described arrangement for producing the prosthesis comprises a shape determination device and a machining device for the actual production of the dental prosthesis, and an electronic data processing (EDP) installation. The EDP installation couples the shape determination device with the machining device, and also includes a memory unit for the results of the shape determination device, and a control unit for controlling the machining device. U.S. Pat. No. 6,287,121 primarily relates to a three serial module arrangement consisting of the shape determination device, EDP installation and machining device. All control and monitoring functions take place in the EDP installation, so that the shape determination device and the machining device need not have individual EDP units. This provides central control and monitoring of the entire production of the dental prosthesis at the EDP installation. Such an arrangement may be efficient for cases where only one machining device is needed. However, such an arrangement may prove disadvantageous in terms of efficiency for relatively large scale production of dental prostheses, e.g. in a production lab having a plurality of machining devices connected in a network with various workstations. In such a network, one may have a plurality of machining jobs, each corresponding to a particular dental prosthesis to be machined and may want to have the machining devices run independently with minimal user intervention. Thus, a system and method specifically suited for such applications would be desirable.

WO 01/37756 discloses an arrangement for a system for manufacturing dental products having a plurality of production units. The manufacturing system comprises various coordination units which receive and register orders from different customers. The coordination units distribute the orders to production units. The various units are updated by data replications in conjunction with changes to system functions, system application and system structure. The data contained in the databases of the production units are entered in memory elements which are arranged for accessing program contents when executing data replications via one or more interfaces. In the arrangement described, a production job for a particular dental product is assigned to a particular production unit by one of the coordination units. The data is then replicated from the coordination unit to that particular production unit.

There are some practical disadvantages associated with such an arrangement. For example, if a particular production unit becomes disabled or inoperative after assignment of the production jobs, the production jobs have to be re-assigned to another production unit. Further, when manufacturing dental prostheses, it is desirable to tailor the machining of the prosthesis to the material characteristics of the material to be machined. To this end, a particular material blank having certain material characteristics may be assigned to a particular prosthesis or production job. If the production job is assigned to a particular production unit for machining, the operator has to make sure that the material blank is placed in the production unit assigned to that production job. If the material blank is placed in the wrong production unit, delays would be caused in the manufacturing process.

Hence, there is a need for a more flexible and robust method and system for manufacturing dental prostheses in an environment having a plurality of production devices. It would be advantageous to provide a system in which it is not necessary to allocate a particular production unit for a particular production job, so that inconveniences associated with such allocation can be eliminated and production jobs can be done in a more autonomous fashion.

SUMMARY OF THE INVENTION

The present invention provides systems and methods that are particularly suitable for manufacturing dental prostheses in an arrangement having a plurality of machining devices. A system according to the present invention comprises essentially at least one workstation having data processing means configured for designing a dental prosthesis using a digital image of a situation of a person's teeth area and a plurality of machining devices for machining the framework for the dental prosthesis from a material blank using machining data generated at the at least one workstation, wherein the machining devices of the system are configured to read an identification code associated with the material blank and to retrieve the machining data corresponding to the identification code of the material blank.

The system may further comprise at least one scanning means for producing a digital image of the situation of a person's teeth area. For example, a scanning means can be provided which can produce a digital image of the situation of a person's teeth by directly scanning an area of a person's teeth or by scanning a working model of an area of a person's teeth. The situation of a person's teeth area refers to the area of the person's teeth, in which the dental prosthesis should be placed.

In the case where a working model is scanned, a working model is provided by a dentist, a dental technician, or other customer. The working model is normally based on an impression made from an area of a person's teeth, in which the dental prosthesis should be placed.

The working model is preferably placed within the scanning means where a digital image is made of the working model. The digital image representing the working model is received by the data processing means of a workstation. Preferably, the data processing means uses a CAD/CAM modeling software, such as Lava™ System (commercially available from 3M-ESPE AG, Seefeld, Germany) to design a framework for the dental prosthesis using the digital image as a basis.

For manufacturing the dental prosthesis, a material blank is typically used. The material blank can be any biocompatible material that is suitable for use in dental prosthetic applications. For example, suitable biocompatible materials may comprise polymer-based materials, precious metals and titanium. Preferably, the material blank is a pre-sintered ceramic, such as pre-sintered zirconium oxide or zirconia, respectively. The material blank may be in any suitable form for machining. For example, the material blank may be in the form of a cylindrical solid block.

Preferably, a material unit is used for securely holding the material blank during machining. Each material unit has a unique identification code which identifies the material unit. This identification code may be a serial number or any code which allows the material unit to be singularly identified. Preferably, the material unit also has a lot identification number which provides information on the characteristics of the material of the blank. For example, the lot identification number could indicate information on the manufacturing of the material and sintering shrinkage properties. This information could be used for designing the dental prosthesis and for determining the specific machining path instructions for the machining devices. Machining could then be tailored for each material blank which in turn provides greater accuracy in the machining process and inevitably an optimal fit for the dental prosthesis.

For each dental prosthesis to be designed and machined, a machining job is established for machining the framework for the dental prosthesis. The machining job is represented electronically by machining data comprised in a machining data file or files. The machining data indicates the machining path instructions and the material unit assigned to that machining job. The machining path instructions are based on the desired parameters for the prosthesis and the material characteristics of the material blank. The machining path instructions can be determined using CAM software.

Each machining device comprises data processing means having a storage unit for storing machining data files and preferably a receiving means for receiving a plurality of material units. The material unit can comprise a means for ensuring proper orientation of the material unit in the receiving means of the machining device. The machining device has reading means for reading the identification code of the material unit. Once the identification code of the material unit is read, the machining device is designed to retrieve the machining data associated with the identification code of the material unit. This is particularly advantageous in that it is not necessary for the operator to place the material unit in a particular machining device or for machining data to be pre-assigned to a particular machining device. This also avoids errors associated with placing the material unit in the wrong machining device. Also, if a machining device is disabled, machining data files do not have to be re-assigned to a different machining device. The operator only has to place the material unit in another machining device. Machining jobs can be completed in a more automated fashion.

The machining device may be any suitable machining device that provides appropriate machining of the material blank to form the framework for a dental prosthesis. Such machining devices may include milling devices, grinding devices laser devices and the like. The machining device is preferably configured to machine the material blank according to the instructions in the machining data file(s) in order to form a dental prosthesis. Preferably, the machining device is so configured that a plurality of material units can be loaded, and finished material units for dental prostheses can be removed while machining continues. Further, the machining device is preferably configured to orientate the material units for machining and to change machining tools according to the specifications of the machining data without intervention from an operator.

In one aspect of the invention, the machining data files generated by a workstation are first stored in a central storage. For example, the central storage could be a network attached server or the like. Each machining device and each workstation has access to the central storage. Once a machining device of the system reads the identification code of a material unit, the data processing means of the machining device is configured to search for the corresponding machining data file in the central storage. The machining device then machines the framework of the prosthesis from the material blank as the machining data is being read from the central storage. After the dental prosthesis has been machined, the machining data is then preferably deleted from the central storage.

In a second aspect of the invention, the machining device is configured to first save the machining data file in the storage unit of the device and then machine the material blank as the machining data file is read from its own storage unit. This is particularly advantageous in that the machining is performed independent of the central storage. For instance, if the central storage means was disabled, it would not affect the machining process of a blank being instantaneously machined. After the machining of the blank is complete, the corresponding machining data file is preferably deleted from the central storage and the storage unit of the machining device.

A third aspect of the invention relates to a product for managing the machining data files. The product has code designed to ensure proper deleting, retrieving and saving of the machining data files in the machining devices, workstations and central storage of the system. For example, the product can have code to ensure that the machining data files are deleted when the corresponding machining job is completed, especially in cases when components of the system are inactive at the time of file deletion.

In a fourth aspect of the invention, a central storage is not used. The data processing means of the workstation is configured to distribute all machining files generated on its computer to all other computers in the system, e.g. to the data processing means of other workstations and to the storage units of each machining device. After the material blank has been successfully machined, the data processing means of the machining device is configured to preferably place a request to delete the corresponding machining data files from the other computers in the network, for example by writing the identification code of the material unit into a designated file. The files in the designated file are automatically deleted from all storage locations in the system, e.g. from the storage means of the workstations and the storage units of the machining devices. This aspect of the invention would also be insensitive against a possible network failure of the system during machining.

A fifth aspect of the invention relates to a product for managing machining data files in a system according to the fourth aspect of the invention. For example, such a product could have code to make sure that files are properly copied and preferably deleted on all computers of the network and to take into account that not all computers may be running at the same time or all the time.

With regard to the various described aspects of the invention, it should be noted that the method steps do not have to be in the specific order described in the preferred embodiments and figures. For example, the step of generating the machining data for a particular blank may take place after or simultaneously with the step of placing the material blank in a machining device or the step of the machining device reading the identification code.

BRIEF DESCRIPTION OF THE DRAWINGS

Preferred embodiments of the present invention will be further described by the following description and drawings.

DETAILED DESCRIPTION

Figure 1:
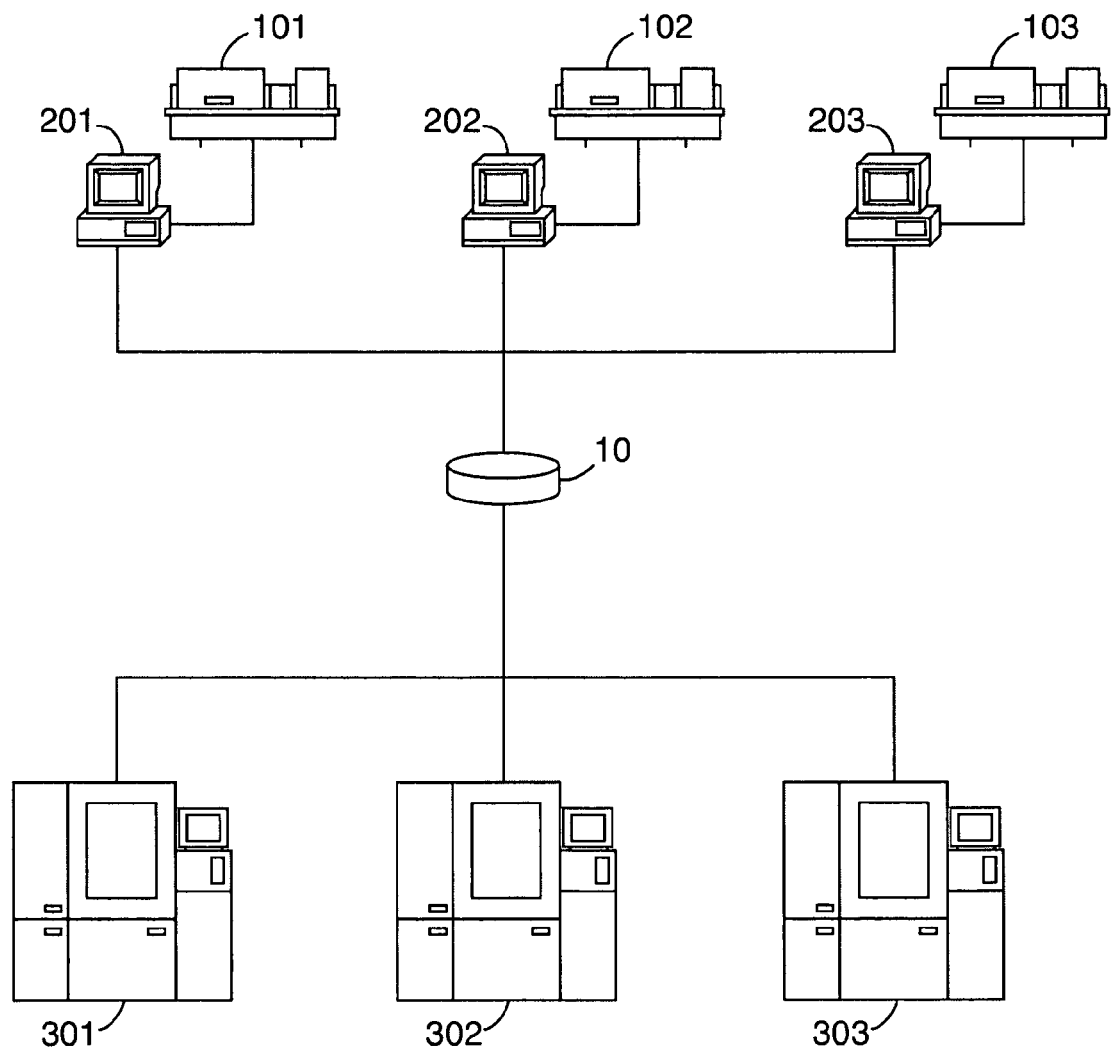
FIG. 1 is a diagram of a system according to the first and second aspects of the invention.
Figure 5:
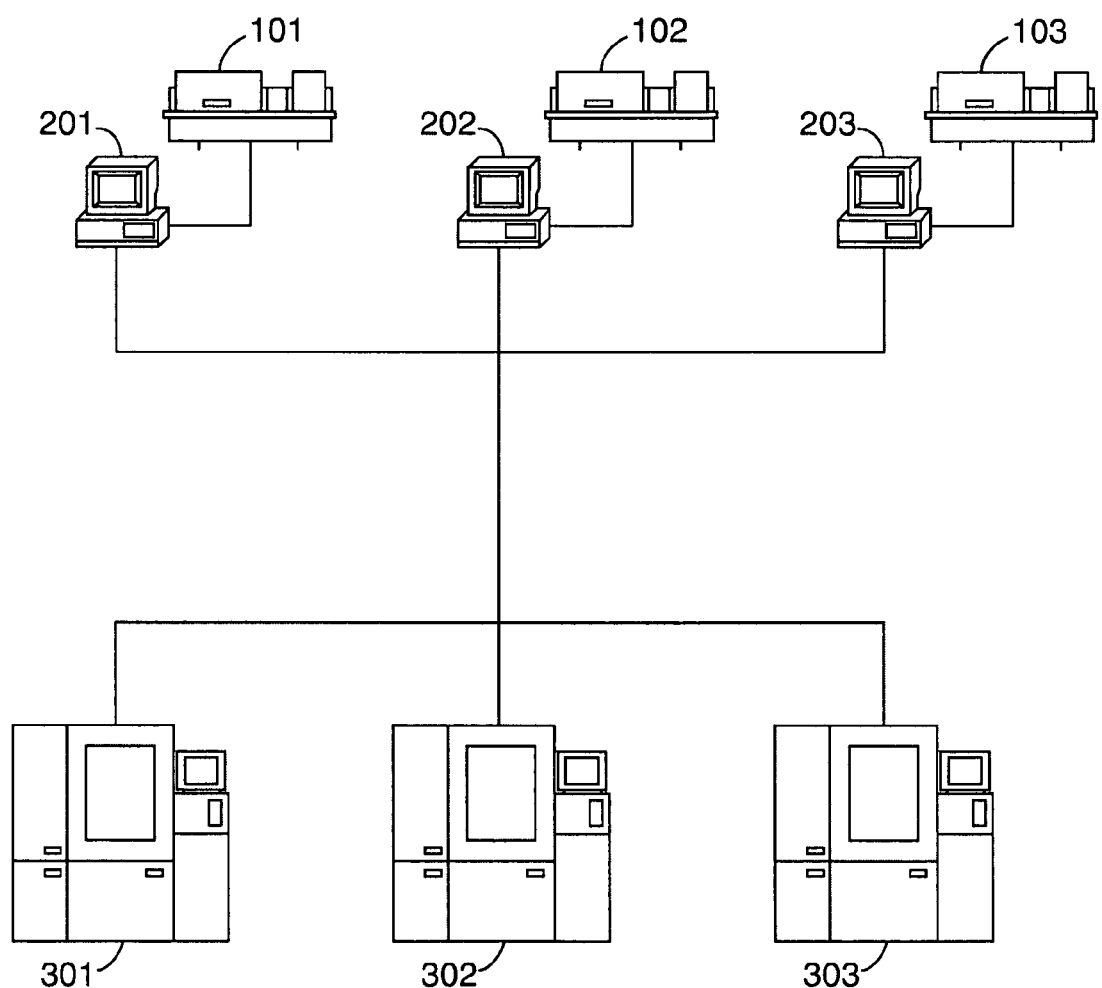
FIG. 5 is a diagram of a system according to the fourth aspect of the invention.

Referring to FIGS. 1 and 5, the system using the method of the present invention generally comprises at least one workstation 201, 202, 203 and a plurality of machining or milling devices 301, 302, 303, preferably forming a local area network or the like. The system may further comprise at least one scanning means 101, 102, 103 electronically connected to at least one of the workstations 201, 202, 203.

The scanning means 101, 102, 103 is configured to scan a model representing the area of a person's teeth in which the dental prosthesis should be placed and to form a digital image of the model. The scanning means 101, 102, 103 is preferably a non-contact 3-D optical scanner.

The workstation 201, 202, 203 comprises an electronic data processing means. Preferably, the workstation is a computer having storage means, a data processor, a monitor, keyboard, mouse and/or touchpad or the like. The data processing means of workstation 201, 202, 203 is configured to store and process digital images received from a scanning means or other external source. Other external sources could include digital images of situations of teeth received via modem, network or read from external storage media. The digital images are processed using CAD/CAM software for designing dental prostheses and for determining the milling data. For example, the dental prosthesis can be designed using a CAD modeling software such as Lava™ System (commercially available from 3M-ESPE AG, Seefeld, Germany). For each dental prosthesis to be designed and milled, a milling job is established for milling the framework for the dental prosthesis. The milling job is represented electronically by milling data comprised in a milling data file or files. The milling data file indicates the milling path instructions and the material blank assigned to that milling job. The milling path instructions are based on the desired parameters for the prosthesis and the material characteristics of the material blank. Preferably, the milling path instructions are determined using the CAM software, for example LAVA™ CALC software (commercially available from 3M-ESPE AG, Seefeld, Germany).

The material blank for the dental prosthesis consists of a biocompatible material. Preferably, the material blank consists of a pre-sintered ceramic material. Most preferably, the material blank consists of pre-sintered zirconium oxide. The material blank may be in any suitable form for milling. For example, the material blank may be in the form of a cylindrical solid block.

Figure 2:
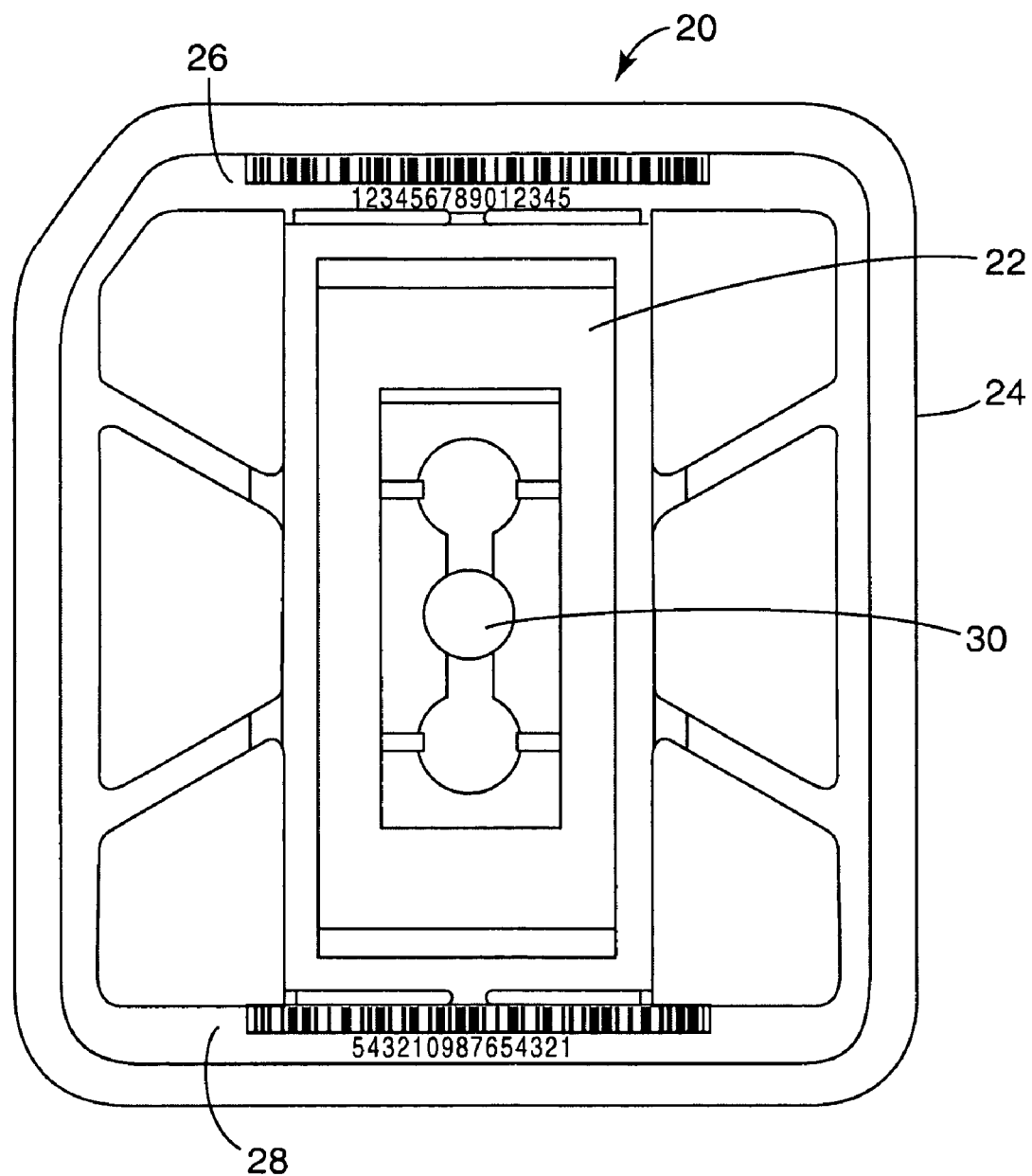
FIG. 2 is an example of a material unit used in the present invention.

Preferably, the material blank 22 is contained in a material unit 20 having the form shown in FIG. 2. The material unit serves to securely hold the material blank during machining or milling. Further, the material unit may have codes or numbers identifying the material blank and its material characteristics. Other suitable material units are described in WO 01/97707 (assigned to 3M-ESPE AG, Seefeld, Germany).

In FIG. 2, the material unit 20 comprises a material blank 22 and a support body 24 for holding the material blank 22. In the example shown, a framework for a dental prosthesis 30 has been milled from the material blank 22. Further, the material unit 20 has a unique identification code 26. Each material unit has a different identification code. This identification code can be a serial number or any code which allows the material unit to be singularly identified. At the workstation 201, 202, 203, a material unit is assigned to each milling job for a dental prosthesis and is associated with milling data for that particular material unit.

Further, the material unit 20 may comprise a material lot number or code 28 which indicates material properties and manufacturing characteristics specific to that particular material blank 22 contained in the material unit 20. Such information could be useful, for example, in calculating sintering shrinkage or suitable machining tools.

The machining or milling devices 301, 302, 303 mill the material blank 22 in order to form the framework of the dental prosthesis 30. The milling devices 301, 302, 303 are configured to receive a plurality of material units 20, for example in a loading area or the like. Each milling device 301, 302, 303 has a data processing means including a storage unit for storing milling data files and reading means for reading the identification codes 26 of the material units 20. The milling data file contains milling path instructions for the milling devices 301, 302, 303.

Figure 3:
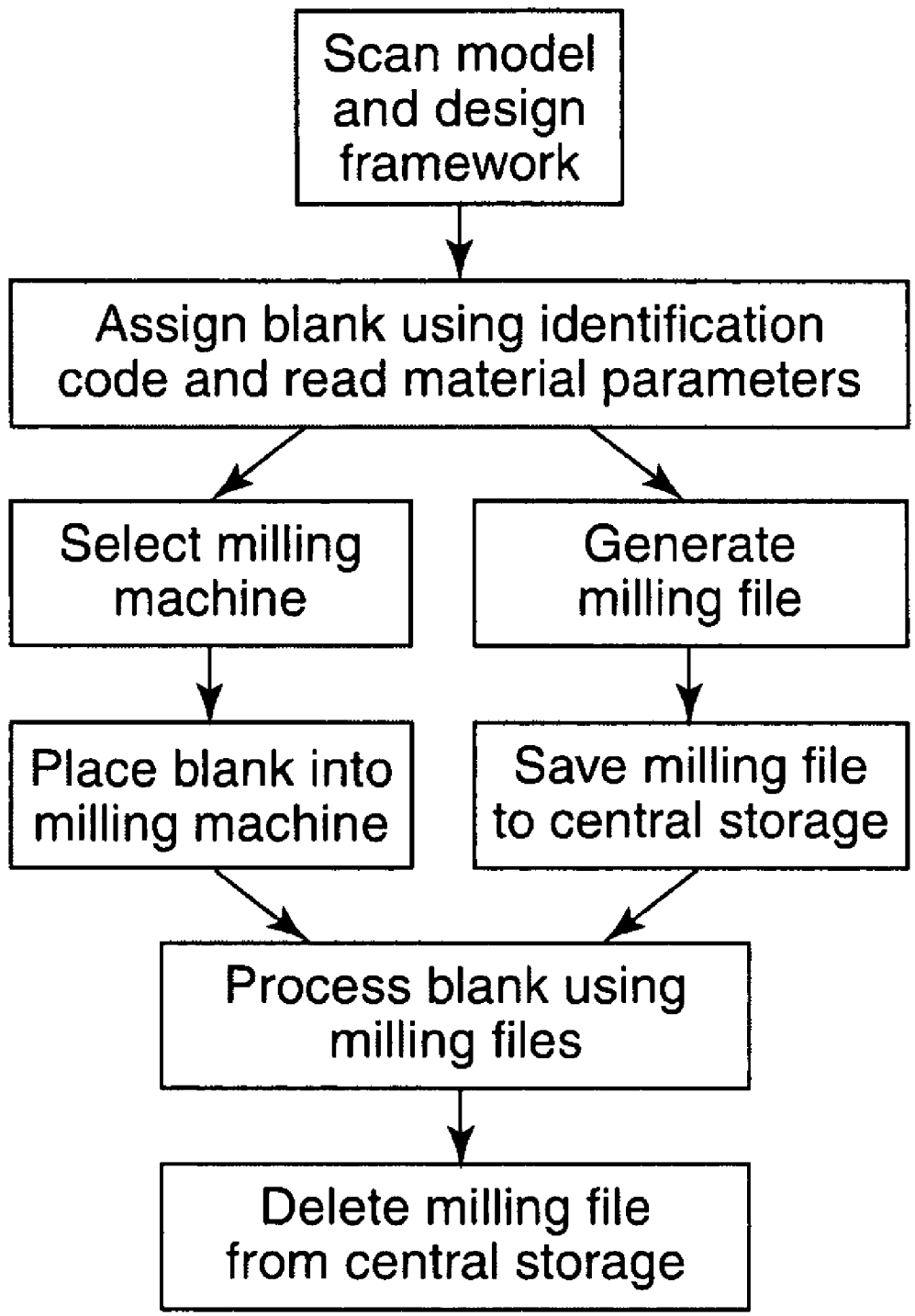
FIG. 3 is a flow chart of a method according to the first aspect of the invention.

FIG. 3 shows a flow chart of a method according to the first aspect of the invention. In this aspect, the milling data files generated by workstation 201, 202, 203 are first stored in a central storage 10 as shown in FIG. 1. For example, the central storage 10 could be a network attached server or the like. Each milling device 301, 302, 303 and each workstation 201, 202, 203 has access to the central storage 10, thereby being able to save to, retrieve from or delete files from the central storage 10. Once a milling device 301, 302, 303 reads the identification code 26 of a material unit 20, the data processing means of the device 301, 302, 303 is configured to search for the corresponding milling data file in the central storage 10. The milling device 301, 302, 303 then mills the framework of the prosthesis 30 from the material blank 22, as the milling data file is being read from the central storage 10. After the framework for the dental prosthesis 30 has been milled, the milling data file is then preferably deleted from the central storage 10. This aspect of the invention is particularly advantageous in that the milling data file does not have to be previously assigned at the workstation 201, 202, 203 to a particular milling device 301, 302, 303. Material units 20 can be placed in any milling device 301, 302, 303 of the system.

Figure 4:
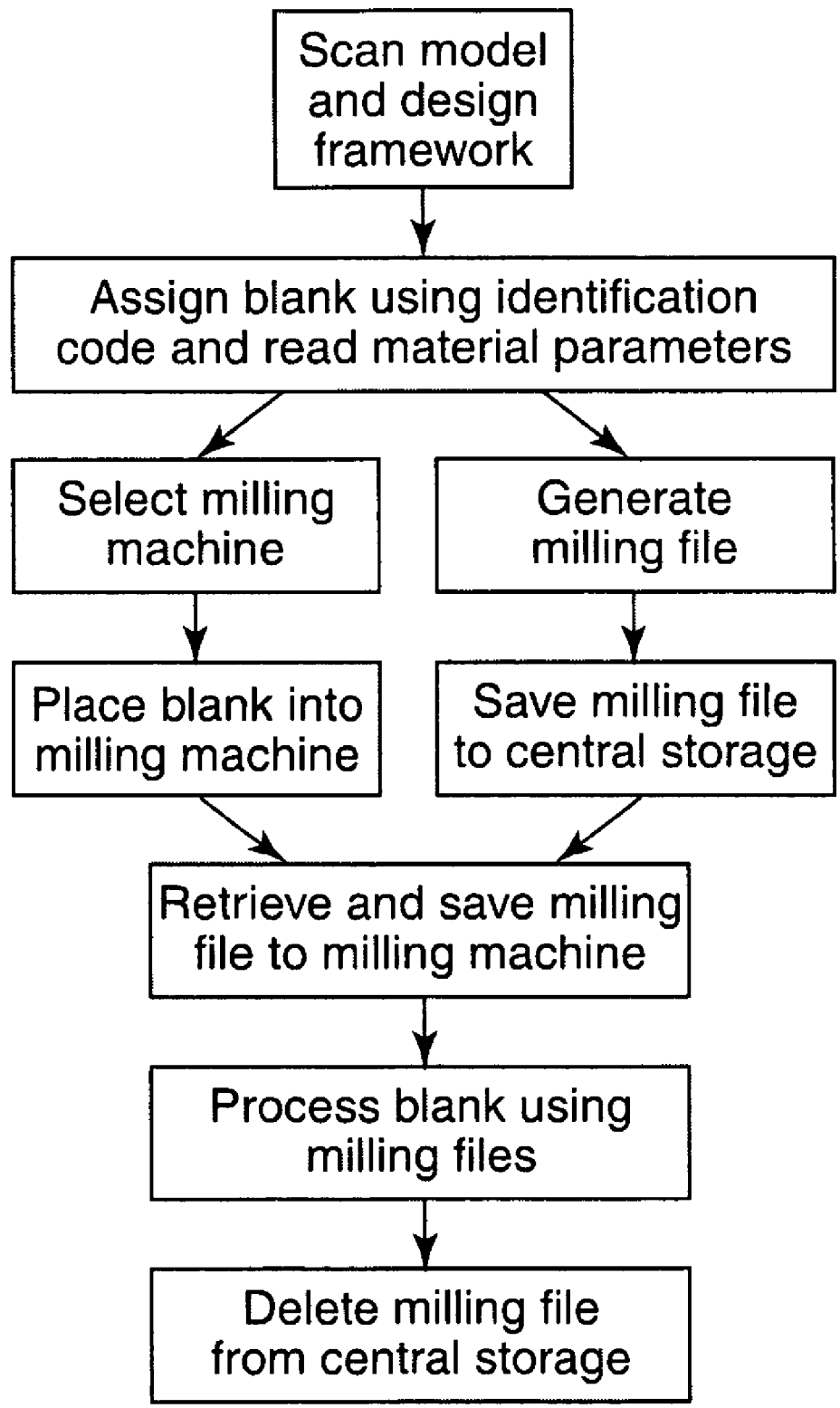
FIG. 4 is a flow chart of a method according to the second aspect of the invention.

FIG. 4 shows a flow chart of a method according to the second aspect of the invention. In this aspect, the milling device 301, 302, 303 is configured to first save the milling data file in the storage unit of the device 301, 302, 303 and then mill the material blank 22 as the milling data file is read from its own storage unit. This is particularly advantageous in that the milling is performed independent of the central storage 10. After the milling of the blank 22 is complete, the corresponding milling data file is preferably deleted from the central storage 10 and the storage unit of the milling device 301, 302, 303.

The third aspect of the invention relates to a product for managing the milling data files using methods and systems according to the first and second aspect of the invention. The product has code designed to ensure proper deleting, retrieving and saving of the milling data files in the milling devices 301, 302, 303, workstations 201, 202, 203 and central storage 10 of the system. The system of the invention may also be accessed externally, for example by providing modem connection or the like to the central storage 10 and/or workstations 201, 202, 203.

Figure 6:
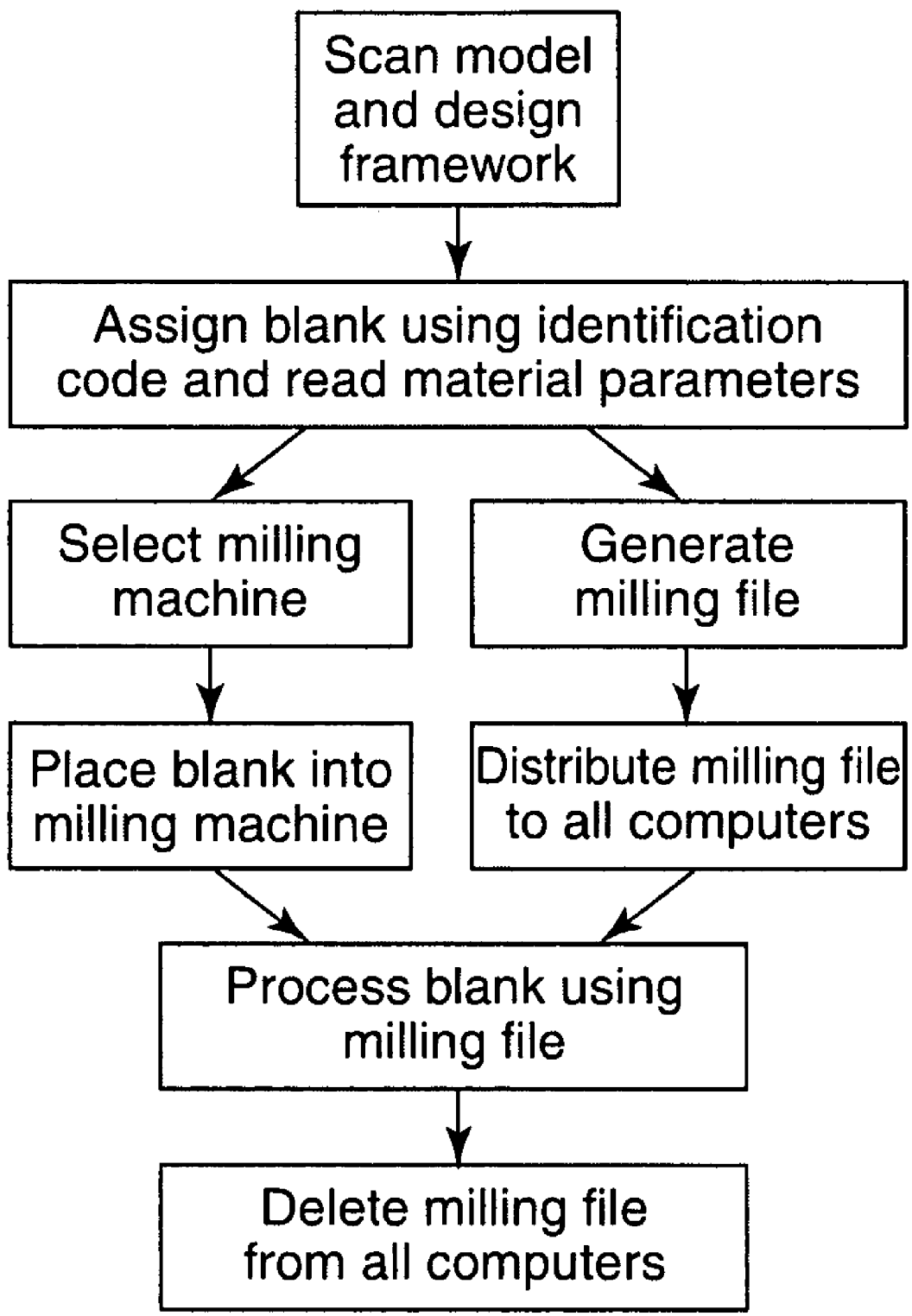
FIG. 6 is a flow chart of a method according to the fourth aspect of the invention.

FIGS. 5 and 6 relate to the fourth aspect of the invention, wherein a central storage is not used. The data processing means of the workstation 201, 202, 203 is configured to distribute all milling data files generated on its computer to all other computers in the network. After successful milling of the material blank 22 of a material unit 20, the data processing means of the milling device 301, 302, 303 is preferably configured to place a request to delete the corresponding milling data files for the material unit 20, for example by writing the identification code 26 of the material unit 20 into a designated file. Preferably, the milling data files in the designated file are read and automatically deleted from all storage locations in the system. The method of this aspect also comprises steps to take into account that not all computers may be running at the same time or all the time. For example, such steps could comprise maintaining lists of the files copied and deleted on all computers. A solution like this would also be insensitive against a possible network failure during milling.

The fifth aspect of the invention relates to a product for managing milling data files in a system according to the fourth aspect of the invention.

The various embodiments presented in the specification are used for the sake of description and clarification of the invention, and thus should not be interpreted as limiting the scope of the invention as such. Moreover, the present invention is realized by the features of the claims and any obvious modifications thereof.

LIST OF REFERENCE NUMERALS 101, 102, 103 scanning means
201, 202, 203 workstation
301, 302, 303 milling device
10 central storage
20 material unit
22 material blank
24 support body
26 identification code
28 material lot number
30 framework for a dental prosthesis

The invention claimed is:

1. A method for manufacturing a dental prosthesis, the method comprising:
providing a system having at least one workstation and a plurality of machining devices;
designing a framework for the dental prosthesis based on a digital image of a situation of an area of a person's teeth;
assigning a material blank for said framework, said material blank having an identification code associated therewith;
generating electronic machining data having content for providing machining path instructions for forming said framework in a machining device;
storing said machining data in a central storage of the system;
placing said material blank in a selected machining device of the plurality of machining devices;
said selected machining device reading said identification code of said material blank, retrieving said machining data corresponding to said identification code; and
said selected machining device machining said material blank using the content of said machining data.

2. The method of claim 1, further comprising:
deleting said machining data corresponding to said identification code.

3. The method of claim 1, wherein after said machining device reads said identification code of said material blank, said machining data corresponding to said identification code is retrieved from the central storage and saved in a storage unit of said selected machining device before machining starts.

4. The method of claim 3, wherein after machining of said material blank is complete, the machining data is deleted from said central storage and from said storage unit of said selected machining device.

5. The method of claim 1, further comprising:
saving said machining data to storage units of at least one workstation and/or at least one machining device of the system.

6. The method of claim 5, wherein after machining of said material blank is complete, said selected machining device requests a deletion of said machining data corresponding to said blank from the storage units of each workstation and each machining device of the system.

7. The method of claim 1, wherein the step of generating electronic machining data is after the step of placing said material blank in a machining device or after the step of said machining device reading said identification code of said material blank.

8. A system for manufacturing a dental prosthesis comprising:
at least one workstation having data processing means configured for designing a framework of a dental prosthesis using a digital image of a situation of a person's teeth area, said data processing means being configured to assign a material blank for said framework and to generate machining data having content for providing machining path instructions for forming said framework in a machining device, said material blank having an identification code associated therewith; and
a plurality of machining devices for machining the framework for the dental prosthesis from said material blank using said machining data generated at the at least one workstation, each machining device comprising data processing means and reading means for reading said identification code of said material blank; and
a central storage accessible to said at least one workstation and said plurality of machining devices;
wherein once said identification code of said material blank is read by a machining device, said machining device is configured to retrieve said machining data corresponding to said identification code of the material blank.

9. The system of claim 8, wherein said system is configured to delete said machining data after said material blank is machined.

10. The system of claim 8, further comprising at least one scanning means for producing a digital image of a situation of a person's teeth area.

11. The system of claim 9, further comprising at least one scanning means for producing a digital image of a situation of a person's teeth area.

12. The system of claim 8, wherein once said identification code of said material blank is read by a machining device, said machining device is configured to retrieve said machining data corresponding to said identification code from said central storage.

13. The system of claim 9, further comprising a central storage accessible to said at least one workstation and said plurality of machining devices, wherein once said identification code of said material blank is read by a machining device, said machining device is configured to retrieve said machining data corresponding to said identification code from said central storage.

14. The system of claim 10, further comprising a central storage accessible to said at least one workstation and said plurality of machining devices, wherein once said identification code of said material blank is read by a machining device, said machining device is configured to retrieve said machining data corresponding to said identification code from said central storage.

15. The system of claim 8, wherein the at least one workstation is configured to save said machining data to at least one data processing means of the system.

16. The system of claim 9, wherein the at least one workstation is configured to save said machining data to at least one data processing means of the system.

17. The system of claim 10, wherein the at least one workstation is configured to save said machining data to at least one data processing means of the system.

18. The system of claim 12, wherein after machining of said material blank is complete, said machining device is configured to request a deletion of said machining data corresponding to said material blank from each data processing means of the system.

* * * * *